(12) United States Patent
Marx

(10) Patent No.: US 7,930,193 B2
(45) Date of Patent: Apr. 19, 2011

(54) SYSTEMS AND METHODS FOR WORKFLOW PROCESSING

(76) Inventor: James G. Marx, Las Vegas, NV (US)

( * ) Notice: Subject to any disclaimer, the term of this patent is extended or adjusted under 35 U.S.C. 154(b) by 0 days.

(21) Appl. No.: 12/726,314

(22) Filed: Mar. 17, 2010

(65) Prior Publication Data

US 2010/0169116 A1 Jul. 1, 2010

Related U.S. Application Data

(63) Continuation of application No. 12/343,408, filed on Dec. 23, 2008.

(60) Provisional application No. 61/016,892, filed on Dec. 27, 2007.

(51) Int. Cl.
*G06Q 10/00* (2006.01)
(52) U.S. Cl. ................................. 705/2; 705/3
(58) Field of Classification Search ............ 705/2–3
See application file for complete search history.

(56) References Cited

U.S. PATENT DOCUMENTS

| | | | |
|---|---|---|---|
| 5,469,353 A | 11/1995 | Pinsky et al. | |
| 5,557,515 A | 9/1996 | Abbruzzese et al. | |
| 5,655,084 A | 8/1997 | Pinsky et al. | |
| 5,909,669 A | 6/1999 | Havens | |
| 5,987,460 A * | 11/1999 | Niwa et al. ............. | 1/1 |
| 6,260,021 B1 | 7/2001 | Wong et al. | |
| 6,519,632 B1 | 2/2003 | Brackett et al. | |
| 6,569,097 B1 | 5/2003 | McMorrow et al. | |
| 6,669,482 B1 | 12/2003 | Shile | |
| 6,678,703 B2 * | 1/2004 | Rothschild et al. ............. | 1/1 |
| 6,746,398 B2 * | 6/2004 | Hervy et al. ............. | 600/300 |
| 6,762,429 B2 | 7/2004 | Aonuma | |
| 6,895,128 B2 | 5/2005 | Bohnenkamp | |
| 6,931,270 B2 | 8/2005 | Daft et al. | |
| 7,189,205 B2 | 3/2007 | McMorrow et al. | |
| 7,200,612 B2 | 4/2007 | Brady et al. | |
| 7,257,189 B2 | 8/2007 | Modica et al. | |
| 7,260,249 B2 | 8/2007 | Smith | |
| 7,289,825 B2 | 10/2007 | Fors et al. | |
| 7,298,876 B1 | 11/2007 | Marshall et al. | |
| 7,331,925 B2 | 2/2008 | McMorrow et al. | |
| 7,366,676 B2 | 4/2008 | Evertsz | |

(Continued)

FOREIGN PATENT DOCUMENTS

CA 2450409 A1 12/2002

(Continued)

OTHER PUBLICATIONS

Roelofs, A.A.J., et al., Effect of soft-copy display supported by CAD on mammography screening performance, Eur Radiol (2006) 16: 45-52.

(Continued)

*Primary Examiner* — Robert W Morgan
*Assistant Examiner* — Reginald Reyes
(74) *Attorney, Agent, or Firm* — Knobbe, Martens, Olson & Bear LLP

(57) ABSTRACT

Systems and methods for processing a workflow are disclosed. Certain embodiments allow prescreened data to be inserted into a workflow. A user's interpretation of prescreened data can be compared with previously obtained characteristics, enabling the user's interpretive output to be monitored and improved. The disclosed systems and methods have applications including, but not limited to, training, performance analysis, process improvement, and data analysis and data mining in workflows.

18 Claims, 9 Drawing Sheets

U.S. PATENT DOCUMENTS

| | | |
|---|---|---|
| 7,418,480 B2 | 8/2008 | Katsman et al. |
| 7,492,970 B2 | 2/2009 | Saito et al. |
| 7,505,557 B2 | 3/2009 | Modica et al. |
| 7,532,942 B2 | 5/2009 | Reiner |
| 2002/0016718 A1 | 2/2002 | Rothschild et al. |
| 2002/0065684 A1 | 5/2002 | Schwalb et al. |
| 2002/0087359 A1 | 7/2002 | Bocionek |
| 2002/0194019 A1 | 12/2002 | Evertsz |
| 2003/0212580 A1 | 11/2003 | Shen |
| 2004/0153340 A1 | 8/2004 | Christ et al. |
| 2005/0256743 A1 | 11/2005 | Dale |
| 2006/0013457 A1 | 1/2006 | Ritter |
| 2006/0031095 A1 | 2/2006 | Barth et al. |
| 2006/0056670 A1 | 3/2006 | Hamadeh |
| 2006/0122482 A1 | 6/2006 | Mariotti et al. |
| 2006/0195339 A1 | 8/2006 | Backhaus et al. |
| 2006/0274145 A1 | 12/2006 | Reiner |
| 2007/0011024 A1 | 1/2007 | Dale et al. |
| 2007/0038474 A1 | 2/2007 | Halsted |
| 2007/0078679 A1 | 4/2007 | Rose |
| 2007/0081699 A1* | 4/2007 | Avinash et al. ............. 382/128 |
| 2007/0203744 A1 | 8/2007 | Scholl |
| 2007/0237380 A1 | 10/2007 | Iwase et al. |
| 2007/0239376 A1 | 10/2007 | Reiner |
| 2007/0239377 A1 | 10/2007 | Reiner |
| 2007/0299687 A1* | 12/2007 | Palmer et al. .................. 705/2 |
| 2008/0021741 A1 | 1/2008 | Holla et al. |
| 2008/0044801 A1 | 2/2008 | Modica et al. |
| 2008/0130839 A1 | 6/2008 | Rogers et al. |
| 2008/0140454 A1 | 6/2008 | Hernandez et al. |
| 2008/0140722 A1 | 6/2008 | Jakobovits |
| 2008/0208634 A1 | 8/2008 | Schwalb et al. |
| 2008/0286734 A1 | 11/2008 | Rottem |
| 2008/0292152 A1 | 11/2008 | Nekrich |
| 2008/0294507 A1 | 11/2008 | Reiner |
| 2008/0312963 A1 | 12/2008 | Reiner |
| 2009/0037319 A1* | 2/2009 | Carstens ....................... 705/37 |
| 2009/0061404 A1* | 3/2009 | Toly ............................. 434/262 |
| 2009/0119283 A1* | 5/2009 | Muehlbauer et al. ............ 707/5 |
| 2009/0172036 A1 | 7/2009 | Marx |
| 2010/0174994 A1 | 7/2010 | Marx |

FOREIGN PATENT DOCUMENTS

| | | |
|---|---|---|
| DE | 10154740 A1 | 6/2002 |
| DE | 10128521 A1 | 1/2003 |
| WO | WO 02/101667 A2 | 12/2002 |
| WO | WO 2008/006389 A2 | 1/2008 |

OTHER PUBLICATIONS

D. Laming & R. Warren, "Improving the Detection of Cancer in the Screening of Mammograms," Journal of Medical Screening, Mar. 2000, pp. 24-30, vol. 7, iss. 1.

International Preliminary Report on Patentability dated Jun. 29, 2010 for International Application No. PCT/US2008/088241.

Berlin, L., Using an automated coding and review process to communication critical radiologic findings: One way to skin a cat, American Journal of Roentgenology, Oct. 2005, vol. 185, pp. 840-843.

Binkhuysen, F.H.B., Impact of PACS on radiologists daily work in western countries, Proceedings of the 2nd International Conference on Image Management and Communication, 1991, pp. 298-305.

Choksi, V.R., et al., Efficiency of a semiautomated coding and review process for notification of critical findings in diagnostic imaging, American Journal of Roentgenology, Apr. 2006, vol. 186, pp. 933-936.

International Search Report dated Apr. 6, 2009 for International Application No. PCT/US2008/088241, Apr. 19, 2009.

Koyama, A., et al., Design and implementation of a remote medical-care supporting system, Proceedings of the 1st International Conference on Complex, Intelligent and Software Intensive Systems (CISIS'07), 2007.

Matsumoto, T., et al., A software system for giving clues of medical diagnosis to clinician, Proceedings of the 15th Symposium on Computer-Based Medical Systems (CBMS 2002), 2002.

Singh, H., et al., Communication outcomes of critical imaging results in a computerized notification system, Journal of the American Medical Informatics Association, Jul./Aug. 2007, vol. 14, Issue 4, pp. 459-466.

Singh, H., et al., Reducing diagnostic errors through effective communication: Harnessing the power of information technology, Journal of General Internal Medicine, 2007, vol. 23, Issue 4, pp. 489-494.

Snel, J.G., et al., A distributed workflow management system for automated medical image analysis and logistics, Proceedings of the 19th IEEE Symposium on Computer-Based Medical Systems (CBMS'06), 2006.

Staccini, P., et al., Evaluation of professional practices in transfusion medicine: Design and implementation of a web-based and tutored ePortfolio, 21st IEEE International Symposium on Computer-Based Medical Systems, 2008.

* cited by examiner

SYSTEMS AND METHODS FOR WORKFLOW PROCESSING

CROSS REFERENCE TO RELATED APPLICATIONS

This non-provisional application is a continuation of U.S. patent application Ser. No. 12/343,408, filed on Dec. 23, 2008, which claims priority from provisional patent application Ser. No. 61/016,892, filed Dec. 27, 2007. The entire contents of each are hereby expressly incorporated by reference.

BACKGROUND

1. Field

This disclosure relates generally to workflows and, more particularly, to training or quality control systems for workflows.

2. Description of the Related Art

Many kinds of industries, businesses, and applications use software systems that manage the flow, progress, rate, or amount of work or data (the "workflow") to and from an office, department, employee, individual, or group of individuals. Healthcare providers such as hospitals use workflow systems like Clinical Information Systems (CIS) and/or Hospital Information Systems (HIS) to manage administrative, financial, medical, and/or laboratory data; Radiology Information Systems (RIS) to store, manipulate, and distribute patient radiological data and imagery; and Picture Archiving and Communication Systems (PACS) for managing medical imaging aspects of the workflow.

Workflows can be used to increase productivity. For example, a primary care physician can recommend that a sick patient have a medical image captured in order to facilitate diagnosis. An MRI acquires the image, and the image is sent to a PACS server. A clinician who specializes in making diagnoses from MRI can access the sick patient's image stored on the PACS system through a diagnostic review workstation. The clinician evaluates the image and makes a diagnosis based on the image, entering the normal or abnormal diagnosis into the workstation's interface. The sick patient's diagnosis is transmitted to a CIS. The primary care physician can later query the CIS and view the diagnostic clinician's diagnosis. The physician presents this diagnosis to the patient. Because the acts of judging the image and making the diagnosis are moved from the primary-care physician to the diagnosing clinician, the primary-care physician has more time to visit with other patients. Furthermore, the diagnosing clinician can efficiently review large numbers of images in series without having to visit with patients. PACS thus increases both the physician's and the diagnosing clinician's productivity.

Although workflows such as CIS, HIS, RIS, PACS, and others can increase productivity and can efficiently store and present data, these workflows have significant drawbacks. Serial workflows, like the diagnosing clinician's workflow described above, typically present a preponderance of normal data and only a very small percentage of abnormal data. This gives rise to a tendency to under-identify abnormal data in a workflow, particularly if the workflow is presented at a rapid pace. For example, a diagnosing clinician can use PACS to review long series of radiological images and diagnose health conditions. Most of the images presented to the diagnosing clinician show normal results. Only a small number of images typically contain abnormalities. After reviewing long series of normal data, however, the diagnosing clinician can become bored, complacent, or fatigued and may tend to under-diagnose, over-diagnose, or misdiagnose subtle and perhaps even startling abnormalities presented in the workflow.

SUMMARY

Systems and methods for processing a workflow are disclosed. Certain embodiments allow prescreened data to be inserted into a workflow. A user's interpretation of prescreened data can be compared with previously obtained characteristics, enabling the user's interpretive output to be monitored and improved.

A system for processing medical image files is provided. The system can comprise some or all of the following components: an unscreened files module, a prescreened files data module, a distribution module, at least one workstation, a comparison module, a feedback module, a cloaking module, a diagnostic output module, a feedback module, an alerting module, and a system monitoring module. For example, in some embodiments, the system comprises the unscreened files data structure, the prescreened files data structure, the distribution module, at least one workstation, the comparison module, and the feedback module. In at least one embodiment, the system comprises the unscreened files data structure, the distribution module, at least one workstation, and the diagnostic output module.

The unscreened data structure can be configured to access unscreened medical image files created by at least one imaging modality. The prescreened data structure can be configured to access prescreened medical image files. The prescreened data structure can be configured to access an associated diagnosis for each of the prescreened medical image files.

A distribution module can comprise some or all of the following components: a selection processor, a workflow queue generation processor, a transmission processor, a distribution monitoring processor, and a distribution override processor. For example, the distribution module can comprise the selection processor and the transmission processor. In at least one embodiment, the distribution module comprises the selection processor, the workflow queue generation processor, and the transmission processor. In at least one embodiment, the distribution module additionally comprises the distribution monitoring processor and the distribution override processor.

The selection processor can be configured to select one or more medical image files from the prescreened files data structure. The selection processor can be configured to select one or more medical image files from the unscreened data structure. The selection processor can configured to select a plurality of medical image files from the prescreened files data structure and the unscreened files data structure. The workflow queue generation processor can be configured to generate a workflow queue. The workflow queue can comprise the selection of medical image files. The transmission processor can be configured to transmit the workflow queue. The transmission processor can be configured to transmit the selection of medical image files. The distribution monitoring processor can be configured to monitor the receipt of the prescreened medical image files.

The distribution override processor can be in communication with the distribution monitoring processor or the selection processor. In some embodiments, the distribution override processor can be in communication with the distribution monitoring processor and the selection processor. The distribution override processor can be configured to prevent the selection processor from selecting from the prescreened files module when the distribution monitoring processor indicates that the receipt of the prescreened medical image files exceeds a threshold value signifying an emergency condition or when an aggregated score (described below) exceeds a threshold value signifying an emergency condition. Other override conditions are also appropriate for use herein.

A workstation can comprise some or all of the following components: a receiving processor, a user input, and a user display. In at least one embodiment, the workstation comprises all of the preceding components. The receiving processor can be configured to receive the workflow queue from the distribution module. The receiving processor can be configured to receive the selection of medical files from the distribution module. The user display can be configured to display the medical image files in the workflow queue or in the selection of medical image files. The user displayed can be configured to serially display the medical image files. The user input can be configure to receive a user diagnosis associated with the medical image file displayed on the user display. The workstation can be configured to receive electronic tag data through the user input. Examples of electronic tag data are, for example, Boolean, binary, ASCII data, and the like. The workstation can be configured to associate the electronic tag data with the medical image file displayed on the user display.

In some embodiments, the system can comprise a central repository. The central repository can be a source of prescreened data. In some embodiments, the prescreened files data structure is configured to access medical image files in the central repository. The central repository can be configured to receive a medical image file associated with above-described electronic tag data.

The comparison module can be configured to receive the user diagnosis from the at least one workstation. The comparison module can be configured to determine whether the user diagnosis is associated with a prescreened medical image file. The comparison module can generate comparison data if the user diagnosis is associated with a prescreened medical image file. In some embodiments, the comparison data can be generated by comparing the user diagnosis with the associated diagnosis.

The feedback module can be configured to receive the comparison data from the comparison module. The feedback module can be configured to transmit the comparison data to the workstation user display.

The cloaking module can be configured to alter origination data associated with prescreened medical image files. For example, the origination data can be altered such that prescreened medical image files appear to originate from the above-mentioned at least one modality.

The diagnostic output module can be configured to receive the user diagnosis from the at least one workstation. The diagnostic output module can generate a score based on a textual evaluation of the user diagnosis. The diagnostic output module can associate the score with the medical image file displayed on the user display.

The feedback module can be configured to receive textual comment data from a physician linked with a certain medical image file, such as the medical image file displayed on the user display. A physician can be linked with a medical image file, for example, using data embedded in a medical image file's header or meta data. As another example, a physician can be associated with the medical image file with a database table. The feedback module can be configured to display the textual comment data on the user display.

The alerting module can be configured receive the score from the diagnostic output module. The alerting process can be configured to transmit an alert to a physician linked with the associated medical image file if the score exceeds a threshold indicating a serious medical condition.

The system monitoring module can be configured to generate an aggregated score with scores received from the diagnostic output module. The aggregated score can be used to trigger override conditions. The aggregated score can be used to adjust the amount of prescreened files distributed to a user. For example, the ratio of unscreened medical image files to prescreened medical image files in the workflow queue can depend on the aggregated score.

In at least one embodiment, a method for processing a workflow is provided. In various embodiments, production workflow data produced by at least one modality, wherein the production workflow data has not been previously characterized, is inserted into a file queue. Prescreened data, wherein the prescreened data has been previously characterized and the prescreened data comprises previous characteristics, is also inserted into the file queue. The file queue is transmitted for an interpretation. The received interpretation of the data comprised in the file queue is evaluated. Based at least in part on the evaluation, the amount of prescreened data inserted into the file queue is adjusted.

In another embodiment, before inserting prescreened data into the file queue, the identification information of the prescreened data is altered so that the prescreened data appears to be produced by at least one modality. The alteration may be performed centrally or locally.

In another embodiment, at least some of the interpreted production workflow data can be reused as prescreened data. The interpretation of some of the production workflow data may be reviewed and characterized. Some of the data may be reused as prescreened data.

In another embodiment, the evaluation of the interpretation of the data comprised in the queue comprises comparing the interpretation of the prescreened data with previous characteristics. The amount of the prescreened data inserted into the file queue may be adjusted based at least in part on the results of the comparison. For example, the amount of prescreened data inserted into the file queue may be increased when the results of the comparison are not successful. In addition, the results the comparison may be communicated to the user.

In another embodiment, the evaluation of the received interpretation of the data comprised in the queue comprises assigning a score based on complexity of characteristics of the production workflow data, with the score being at least in part proportional to the complexity. The adjustment of the amount of the prescreened data inserted into the file queue may be at least in part inversely proportional to the assigned score of the previous work product output.

In another embodiment, the evaluation of the received interpretation of the data comprised in the queue may allow enhancing the use of data analysis and data mining capabilities of the workflow. Data analysis and data mining may be used to improve, forecast, and predict users' accuracy and efficiency.

In another embodiment, at least some of the received interpretation of the data comprised in the file queue may be marked as "unknown," that is data whose interpretation the user is unsure about. At least some of the data marked as "unknown" may be reinserted into the file queue, and transmitted for another attempt at the interpretation by the same or another user.

For purposes of summarizing the embodiments and the advantages achieved over the prior art, certain items and advantages are described herein. Of course, it is to be understood that not necessarily all such items or advantages may be achieved in accordance with any particular embodiment. Thus, for example, those skilled in the art will recognize that the inventions may be embodied or carried out in a manner that achieves or optimizes one advantage or group of advantages as taught or suggested herein without necessarily achieving other advantages as may be taught or suggested herein. The flow charts described herein do not imply a fixed order to the steps, and embodiments of the invention may be practiced in any order that is practicable.

BRIEF DESCRIPTION OF THE DRAWINGS

A general architecture that implements the various features of the disclosed systems and methods will now be described with reference to the drawings. The drawings and the associated descriptions are provided to illustrate embodiments and not to limit the scope of the disclosure. Throughout the drawings, reference numbers are re-used to indicate correspondence between referenced elements. In addition, the first digit of each reference number indicates the figure in which the element first appears.

These and other features will now be described with reference to the drawings summarized below. These drawings and the associated description are provided to illustrate preferred embodiments of the invention, and not limit the scope of the invention.

DETAILED DESCRIPTION

In various embodiments disclosed herein, systems and methods are provided to allow prescreened data to be inserted into a workflow. "Prescreened" is a broad term and is to be given its ordinary and customary meaning to a person of ordinary skill in the art (that is, it is not to be limited to a special or customized meaning). Data can be considered prescreened if they are reviewed and identified as having certain characteristics before they are intentionally inserted into a workflow for later interpretation. A user's interpretation of the prescreened data can be compared to the correct interpretation. The disclosed systems and methods have applications including, but not limited to, training, performance analysis, process improvement, and data analysis and data mining in workflows.

As explained above, it is desirable that a user accurately process data presented in a workflow. However, workflows typically present a preponderance of normal data and only a very small percentage of abnormal data. After reviewing long series of normal data, a user can become bored, complacent, or fatigued and may tend to under-interpret, over-interpret, or misinterpret subtle and perhaps even startling abnormalities presented in the workflow, particularly if the workflow is presented at a rapid pace. Various embodiments include the realization that workflow processing can be improved by inserting prescreened data into the workflow. The user's interpretation of prescreened data can be compared with the correct interpretation, enabling the user's interpretive output to be monitored and improved.

Many types of data network connections are suitable for interconnecting components described herein. Suitable data network connections can be, for example, a local area network (LAN) connection, wide area network (WAN) connection, wireless local area connection (WLAN), the Internet, virtual private network (VPN) connection, secure sockets layer (SSL) connection, or the like. Additionally, a data network connection can be an electronic connection between a keyboard and a computer, between a media reader and a computer, between hardware components in a computer (e.g., a bus connection between a hard drive and module), or the like. References to "transmitting," "communicating," "sending," and the like as used in this description refer to delivering data over a suitable data network connection.

Figure 1:
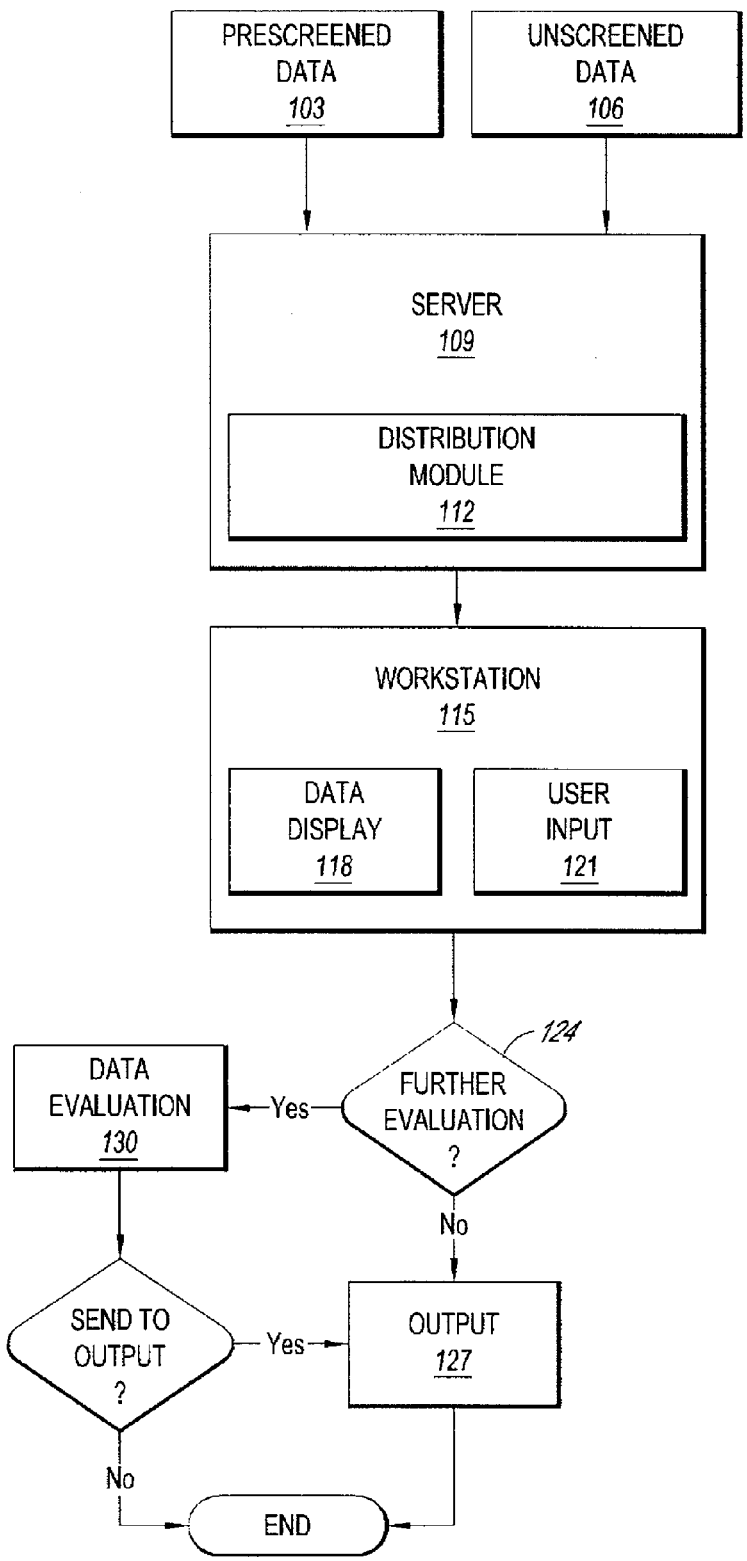
FIG. 1 is a block diagram illustrating a workflow system.

For a more detailed understanding of the disclosure, reference is first made to FIG. 1, which illustrates a workflow system according to at least one embodiment. The system comprises a source of prescreened data 103 and, optionally, a source of unscreened data 106. The prescreened data 103 and unscreened data 106 can be transmitted to at least one user workstation 115 through a server 109. The data processed at the workstation 115 can optionally be transmitted to a decision module 124 to determine whether the data requires further evaluation. Thereafter, the data can be transmitted to an output 127 and/or a data evaluation 130 module.

As previously discussed, "prescreening" can refer to identifying certain characteristics of data before data is intentionally inserted for later review by a user. In contrast, unscreened data 106 is data that has not previously been characterized. "Unscreened" is also a broad term and is to be given its ordinary and customary meaning to a person of ordinary skill in the art (that is, it is not to be limited to a special or customized meaning). An example of unscreened data 106 is production workflow data.

Prescreening can take many forms. For example, prescreening can be a peer review's consensus diagnosis of a patient's medical image file, such as normal, abnormal, cancerous, pre-cancerous, benign, unknown, or uncertain, etc. Prescreening can be a technician's disposition of a semiconductor wafer after photolithography processing, such as normal, closed contacts, pattern lifting, etc. Prescreening can be an evaluation of luggage X-rays, such as safe or unsafe. Prescreening can be a recommendation for an action such as "do not replace the part," "maintain the current temperature," "turn 90° left," "do not collect a sample here," etc., depending on the particular workflow. Prescreening can be a numerical, textual, binary, Boolean value, or the like.

The prescreened data 103 can be transmitted to the server 109 along with the unscreened data 106. In some embodiments, the server 109 can be a central PACS server. The central PACS server can acquire, via a data network connection, unscreened and prescreened DICOM files. Other types of servers that can acquire files from an entity are also suitable. For example, a server can be a central computer on an aircraft that acquires sensor data from a plurality of sub-computers associated with a plurality of sensors via various network connections. The server can comprise a distribution module 112. The distribution module 112 can be configured to distribute the prescreened data 103 and the unscreened data 106 to one or more user workstations 115.

The workstation 115 may include a data display 118 and permit the user to review data. The workstation 115 may also include a user input 121 and permit the user to enter interpretations of data.

A user may be a clinician such as an interpreting radiologist or cardiologist who reviews DICOM files. However, a user may be a business entity, a semiconductor process technician, a luggage inspector, a manufacturing test diagnostician, a pilot, or the like. As mentioned above with reference to FIG. 1, the workstation may include a data display configured to present data for interpretation, and a user input configured to receive interpretations of data.

The interpretation entered in the user input 121 can optionally be transmitted to a decision module 124. The decision module 124 may determine if the evaluated workflow data was prescreened or unscreened workflow data. If the workflow data was prescreened, then the interpretation may be transmitted to a data evaluation module 130, described in more detail below. If the workflow data was unscreened, then the interpretation may be sent to the system output 127. However, as discussed in more detail below, the decision module 124 can evaluate other data characteristics.

System output 127 can be any entity; server, computing device, network of computing devices, storage system (e.g., a backup system or database), display system (e.g. a monitor or printer), workflow or the like that receives users' interpretations of workflow data. System output can be in the same workflow or in a different workflow. Many types of configurations are suitable for system output. For example, system output can be a CIS for a healthcare provider or pool of healthcare providers. In this example, the CIS can receive diagnoses based upon production workflow medical images from users (e.g. clinicians or radiologists) workstations, and the diagnosis is then examined by a physician (e.g. a treating physician). As another example, system output can be a computer onboard an airplane that controls certain flight equipment. The onboard computer can receive a pilot's interpretation of certain sensor readings that the pilot communicates via a keypad or via a speech-interpreting unit.

Figure 2:
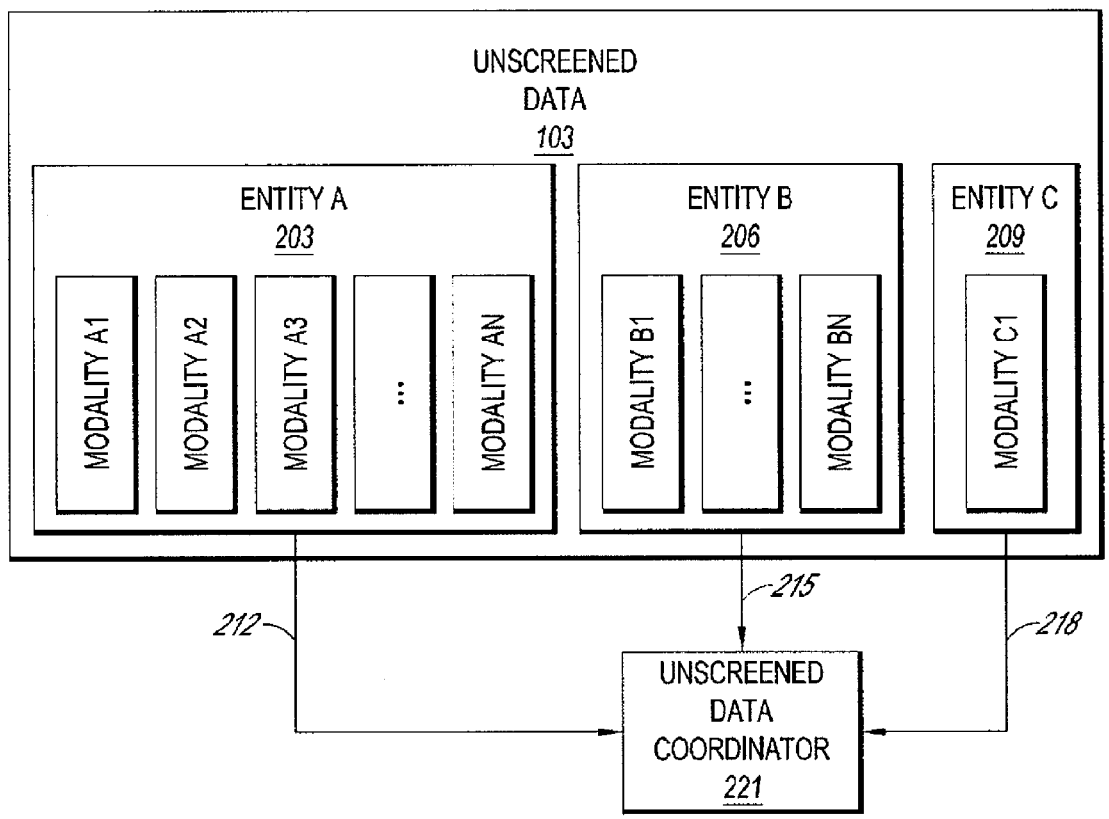
FIG. 2 illustrates sources of unscreened data.

FIG. 2 illustrates sources of unscreened data 103, for example, production workflow data. Entity A 203 and Entity B 206 each comprise a plurality of modalities that produce workflow data. Entity C 209 comprises a single modality. Modalities can be associated with an entity via a suitable connection, such as a data network connection, an electronic connection, a virtual connection, or the like. The entities 203, 206, 209 may transmit production workflow data to an optional unscreened data coordinator 221 (discussed in more detail with respect to FIG. 3) via data network connections 212, 215, and 218.

The entities shown in FIG. 2 (Entity A 203, Entity B 206, and Entity C 209) can be healthcare entities such as hospitals, clinics, imaging centers, medical offices, physicians, or the like. An entity can also be a corporation, airport terminal, semiconductor fabrication laboratory, an assembly line, business unit, network of computers, a single computer, or the like.

In some embodiments, an entity processes the data received from a modality. For example, the entity can format, modify, compress, delete, and/or store data received from a modality. In some embodiments, the entity does not process the data the received from a modality. For example, the entity can be a "virtual entity" that transmits data received from a modality without performing any other processing of the data.

Modalities can be medical imaging devices that generate DICOM files, such CT scanners, MRI scanners, X-ray scanners, DCRs, mammography machines, fluoroscopy machines, etc. A modality can be a video camera, wafer prober, thermocouple, or sensor such as a light, speed, voltage, or altitude sensor. A modality can be a media reader such as a ZIP, floppy, CD, DVD, or other computer drives that reads electronic files stored on computer-readable media. As another example, a modality can be a keypad for entering information into files.

A modality creates "unscreened" data, such as production workflow data. Unscreened data has not been identified as having certain characteristics before the data is inserted into a workflow for a later review by a user. For example, a DICOM file can be considered unscreened if a diagnostic clinician has not yet reviewed the images embedded in the file. A patterned semiconductor wafer can be considered unscreened if the wafer has not yet been reviewed by a technician to identify and/or characterize pattern defects. A piece of luggage can be considered unscreened if the luggage has not yet passed to a TSA screener for evaluation.

Workflow data (that is, unscreened and/or prescreened data) can be binary-format files such as image or sound files or formatted text files. For example, in some embodiments, the data is a DICOM-format file. A DICOM (Digital Imaging and Communications in Medicine) file comprises medical examination images as well as patient and examination information such as patient demographics, patient name, patient age, exam number, exam modality, exam machine name, and exam date in a file header. Data can also be ASCII files such as unformatted text files. Data can also be tangible objects. For example, a photolithocell modality may generate patterned semiconductor wafers.

Figure 3:
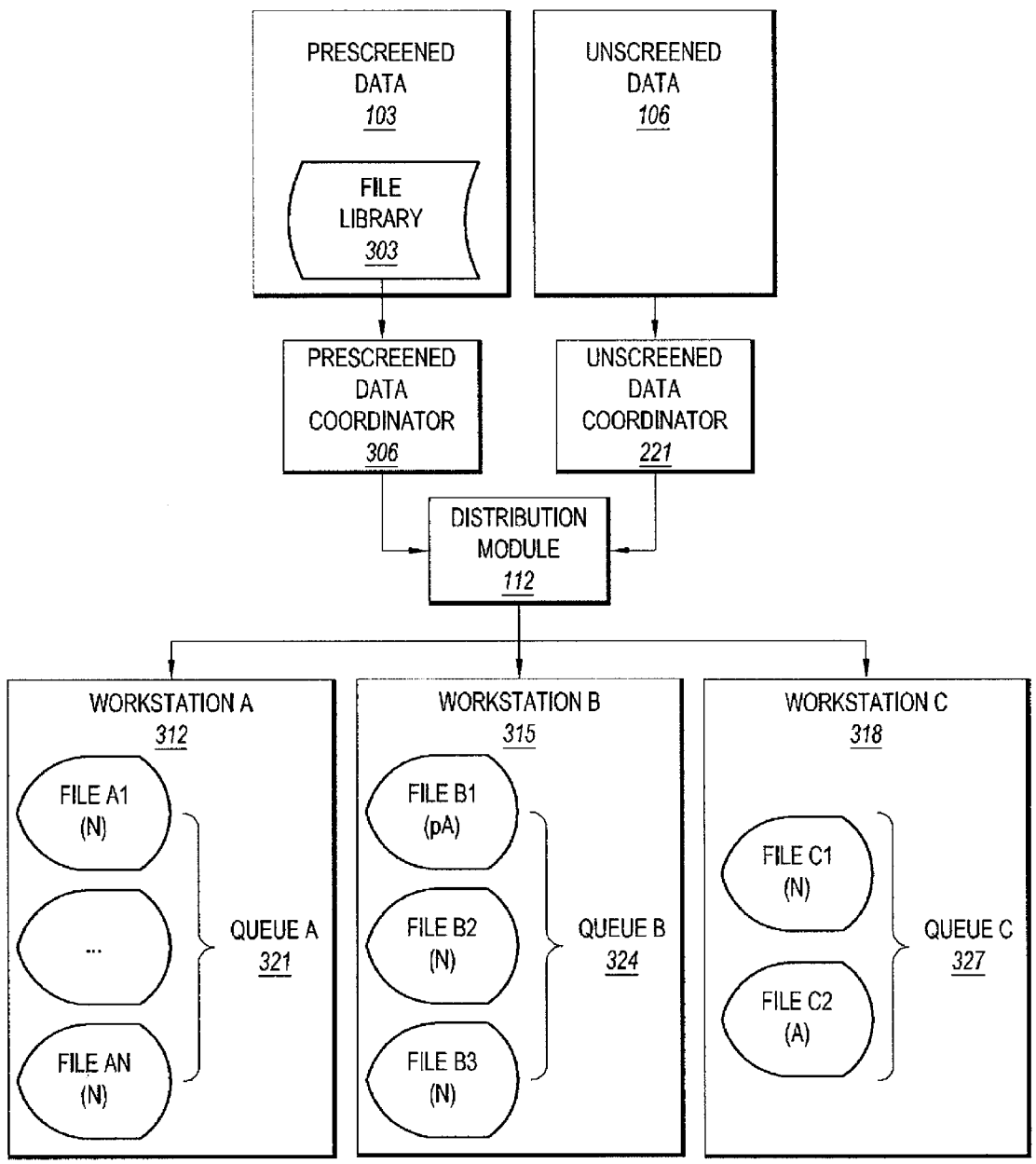
FIG. 3 illustrates insertion of prescreened data into a workflow.

FIG. 3 illustrates an example embodiment comprising prescreened data 103 obtained from a file library 303. FIG. 3 also illustrates operation of the workflow distribution module 112, the prescreened data coordinator 306, and the unscreened data coordinator 221.

In some embodiments, the source of prescreened data 103 comprises one or more file libraries 303. A file library 303 is configured to send prescreened data. A file library 303 can be a database or files on a computer-readable medium such as a ZIP disc, external hard drive, CD, DVD, or the like. A file library can be local or stored on a remote network or server. For example, a file library can comprise prescreened digitized images, X-rays, HL-7 compliant files, etc.; files prescreened by a third-party provider such as a CME (continuing medical education) or other continuing education program, a commercial vendor, a peer review board or program, an Internet web site; or files prescreened by entities comprised by the workflow (for example, a physician from a hospital entity can have certain patient images stored locally on a personal computer).

A file library 303 can be implemented in conjunction with an optional prescreened data coordinator 306. The prescreened data coordinator 306 can communicate with the file library 303, for example, via a data network or other suitable connection. The prescreened data coordinator 306 may be located on the same computer that stores the file library 303 and/or the distribution module 112. Alternatively, the prescreened data coordinator 306 can be a separate local or remote computer.

In certain embodiments, the prescreened data coordinator 306 is configured to coordinate the insertion of prescreened data from the file library 303 into a distribution module 112. The prescreened data coordinator 306 can comprise human decision-makers, such as a case review committee or a peer review committee. Preferably, the prescreened data coordinator 306 comprises a computer system that manages the input and output of data. The prescreened data coordinator 306 can be located on the same computer as the file library 303 and/or distribution module 112 or on a different local or remote computer. Adjustments of the amount of prescreened data to be presented to users may be performed by the prescreened data coordinator 306, and the adjustment may then be transmitted to a distribution module 112. This may result in a centralized system-wide adjustment, and may be performed remotely.

In some embodiments, the prescreened data coordinator 306 can access, select, and/or electronically mark, flag, or otherwise alter data or files obtained from the file library 303 for subsequent distribution by the distribution module 112. Many types of electronic marks are suitable, such as setting a Boolean or binary switch or flag in a file, inserting a switch or flag the file's header (e.g., in a DICOM file header), altering the file name, inserting a particular string, switch, or flag within the file, or the like. In various embodiments, the prescreened data coordinator 306 can move the altered file outside the file library, or the prescreened data coordinator 306 can copy the original file and store the altered file outside the file library.

For instance, a human prescreened data coordinator 306 using a general purpose computer can access a DICOM files stored in a file library 306. The prescreened data coordinator 306 can select a DICOM file and alter the data in the DICOM file header to indicate how the file will be subsequently distributed by a distribution module 112. The distribution module 112 accordingly can be configured to access the DICOM file header to look for certain altered data for distribution instructions.

In some embodiments, the prescreened data coordinator 306 can comprise a database configured to store information about a file in the file library 303, which information can be accessed by the distribution module 112. For example, the prescreened data coordinator 306 can process a DICOM file and access a database table associated with the DICOM file. The data in the table can be altered to indicate how the file will be subsequently distributed by the distribution module 112. For example, the table can be configured to store the file name and information regarding to which user login that file is to be distributed. The distribution module 112 accordingly can be configured to access the table to look for distribution instructions.

In the example shown in FIG. 3, the prescreened data coordinator 306 can mark a file from the file library 303 such that the distribution module 112 will distribute the file to workstation A 312, workstation B 315, and workstation C 318. In another instance, the prescreened data coordinator 306 can electronically mark a file so that the file is distributed only to workstation A 312. The prescreened data coordinator 306 can control a variety of parameters, for example, location, time, order, etc. of the files inserted.

In some embodiments, the prescreened data coordinator 306 marks files according to a predefined set of constraints. For instance, the prescreened data coordinator 306 can mark data such that one file will be distributed to each workstation twice per hour. In some embodiments, the prescreened data coordinator 306 can mark files according to dynamically received and learned events. Dynamic and learned processing will be discussed in more detail below.

The optional unscreened data coordinator 221 can be configured similar to the above-described prescreened data coordinator 306. The unscreened data coordinator 221 can communicate with the source of unscreened data 106, for example, via a data network or other suitable connection. The unscreened data coordinator 221 stores information about unscreened data 106, such as originating entity and or modality, patient ID, primary-care physician, number and location of related images, number and/or identity of diagnosing physicians. The unscreened data coordinator 221 may be located on the same computer that stores the unscreened data 106 and/or the distribution module 112. Alternatively, the unscreened data coordinator 221 can be configured on a separate local or remote computer. In various embodiments, the prescreened data coordinator 221 can be configured to store unscreened data. However, the prescreened data coordinator 221 can also be configured to point to remotely stored unscreened data.

In certain embodiments, the unscreened data coordinator 221 is configured to coordinate the insertion of unscreened data 106 into a distribution module 112. The unscreened data coordinator 221 can comprise human decision-makers, such as primary-care physicians. Preferably, the prescreened data coordinator 221 comprises a computer system that manages the input and output of data.

For instance, a human unscreened data coordinator 221 using a general purpose computer can access a DICOM file stored in a source of unscreened data 106. The unscreened data coordinator 221 can select the DICOM file and alter the data in the DICOM file header to indicate how the file will be subsequently distributed by a distribution module 112. The distribution module 112 accordingly can be configured to access the DICOM file header to look for certain altered data for distribution instructions. In other embodiments, the unscreened data coordinator 221 can comprise a database configured to store information about an unscreened data 106 file, which information can be accessed by the distribution module 112. For example, the unscreened data coordinator 221 can access a database table associated with the DICOM file. The data in the table can be altered to indicate how the file will be subsequently distributed by the distribution module 112. For example, the table can be configured to store information regarding how many workstations the file should be distributed to. The distribution module 112 accordingly can be configured to access the table to look for distribution instructions.

The prescreened data coordinator 306 and/or the unscreened data coordinator 112 can be omitted in various embodiments. For example, the files stored in a file library 303 can be transmitted to a distribution module 112 automatically as part of a subscription service. As another example, unscreened data 106 does not need to have its attributes modified. As further example, the distribution module 112 may be configured to control and/or process files stored in the file library, by using the mechanisms explained above. Alternatively, the file library 303 may be configured to control and/or process stored files.

As explained above, a distribution module 112 can acquire unscreened data 106 (such as production workflow data) and, prescreened data 103. The distribution module 112 distributes, via suitable data network connections, unscreened data 106 and prescreened data 103 to one or more workstations 312, 315, 318 for processing. The distribution module 112 can comprise a computer performing a preprogrammed or dynamic calculation. In some embodiments, the distribution module 112 can comprise a human performing a manual calculation.

The distribution module 112 can operate as a sequential module that retrieves a file upon a request by a workstation. In some embodiments, the one or more workstations 312, 315, 318 can send a request for a file to the distribution module 112. The distribution module can then request the file from a source of unscreened data 106 or the source of prescreened data 103 and send the file to the requesting workstation. The requesting workstation can also request the file from the source of prescreened or unscreened data directly without intermediate processing by the distribution module 112. In some embodiments, the distribution module 112 can select the file from a pool of files comprising unscreened data 106 and prescreened data 103 randomly or according to one or more selection criteria. These selection criteria are described in more detail in this disclosure.

Various embodiments include the realization that processing speed can be improved by creating file queues. As discussed in more detail below, a file queue can be assembled independent of a user's requests for a file. Preferably, a file queue is assembled prior to a user's request for a file. A queue can comprise one or more data items, such as data files, to be processed by a user. A queue can comprise, for example, one, tens, hundreds, or thousands of data items. Preferably, a queue comprises a plurality of data items. An example queue comprises a queue of DICOM files. Queues created and distributed to user workstations need not comprise an identical number of data items. For example, in FIG. 3, queue A 321 comprises N files, queue B 324 comprises three files, and queue C 327 comprise two files. The file queue can be stored on the distribution module 112 or other suitable sever for access by one or more workstations. In some embodiments, the file queue can be transmitted to one or more workstations.

Figure 4:
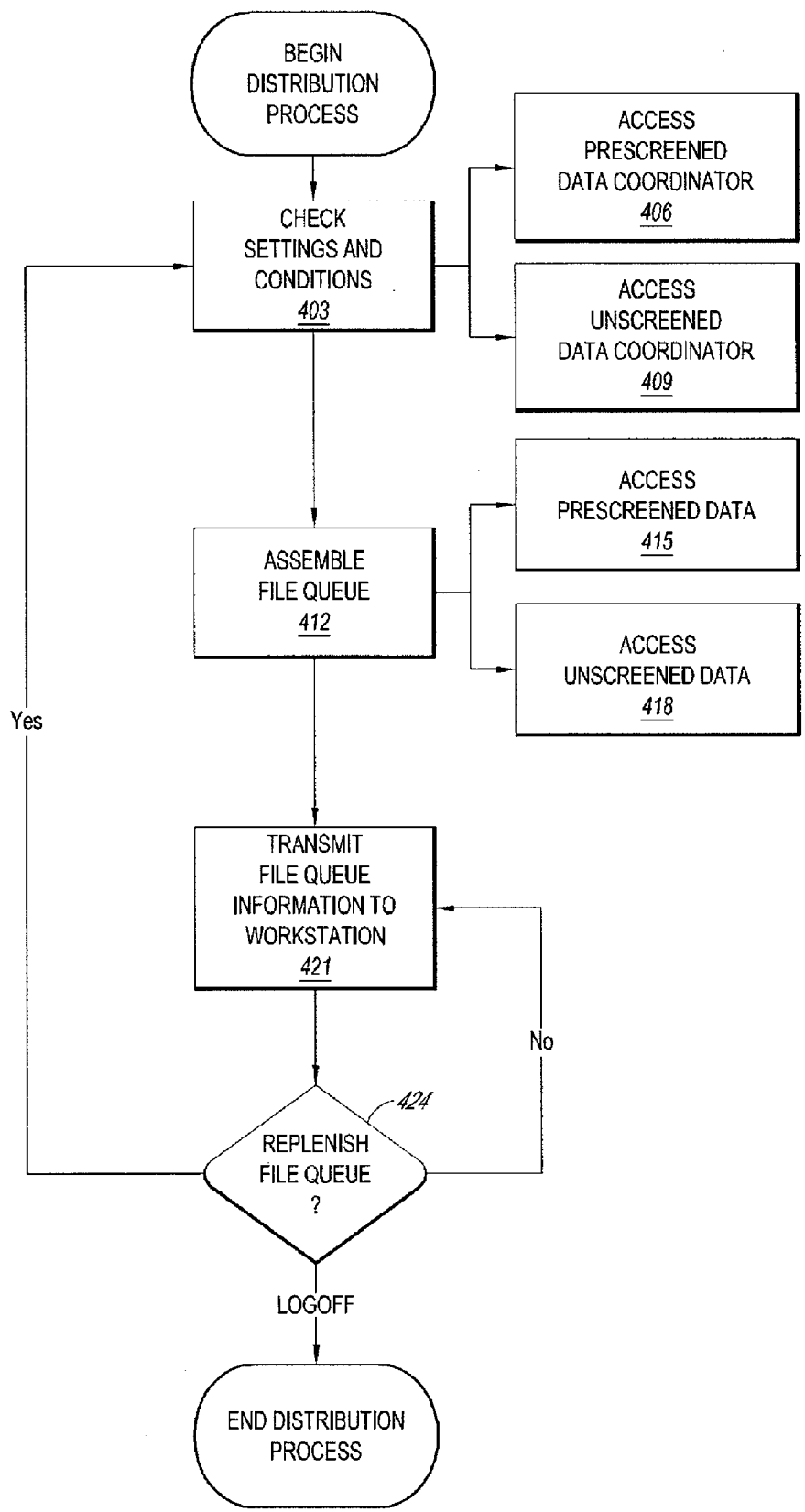
FIG. 4 illustrates operation of a workflow distribution module.

An example distribution process decision tree 400 comprising assembling a single user's file queue is shown in FIG. 4.

The distribution module can optionally check settings and conditions 403. For example, the distribution process can check such as user and process settings, such as time, date, user login information, workstation ID, etc. As another example, a superuser could set a process setting to temporarily or permanently halt the transmission of prescreened data to a single user workstation, to a group of user workstations, or to all user workstations. The process setting could be set locally or by SSL (internet or intranet), by e-mail, instant message, SMS text message, and the like. Of course, additional user, process, and other settings can be useful determining how and/or when to distribute files to workstations and are contemplated for use in the disclosed embodiments.

In some embodiments, the distribution module can check systemic conditions (such as user file load, average processing time, number or rate of incoming unscreened cases, etc.) For example, a systemic condition could be that the backlog of unscreened files not yet interpreted doubles in one hour. Other systemic conditions could be, for example, that one user's queue is 25% shorter than average, one user's queue is replenishing 50% slower than average, one user's queue is 75% shorter than other users' queues, a user has made more than three incorrect interpretations in the last month, etc. Certain embodiments include the realization that detecting systemic conditions could advantageously avoid overburdening users with prescreened data in the midst of a natural disaster, epidemic, terrorist attack, war, or other event that may create large volumes of production workflow data.

As explained above, the distribution module can also optionally access the prescreened data coordinator 406 and/or the unscreened data coordinator 409 for distribution information. For example, as discussed above, the prescreened data coordinator 406 and the unscreened data coordinator 409 can store information regarding which files in the file library are to be distributed to which user(s), at which workstation(s), at which time(s) or date(s).

Using the settings and conditions information, the prescreened data coordinator information, and/or the unscreened data coordinator information, the distribution module 112 can assemble the file queue 412 utilizing a file assembly algorithm. A variety of algorithms are suitable for assembling the file queue. For example, the file assembly algorithm can insert unscreened data and prescreened data at fixed intervals or random intervals.

Preferably, however, the file assembly algorithm is configured to adjust the amount of prescreened data inserted. For instance, the file assembly algorithm can insert more or less prescreened data into a particular user's queue if it determines or is informed that a certain condition or conditions are met, such as a particularly light or heavy file load, more or fewer errors than other users, etc. As discussed above, the file assembly algorithm can evaluate systemic settings or conditions indicating rapidly increasing backlogs in the number of unscreened files to be processed. Accordingly, the file assembly algorithm can temporarily or permanently halt the transmission of prescreened data to user workstations. In certain embodiments, the file assembly algorithm may adjust the amount of prescreened data inserted into the workflow dynamically according to received and/or learned events, such as the richness of a user's interpretive output. This feature is discussed in more detail below.

During or after the process of assembling the file queue 409, the distribution module can access the prescreened data 415 and the unscreened data 418. For example, the distribution module can establish links or pointers to prescreened and/or unscreened files stored remotely. Alternatively, the distribution module can download and store files from the sources of prescreened data and unscreened data. The file queue is then ready for access by the user, and the information (files or pointers) in the file queue can be transmitted to a workstation 421.

Still referring to FIG. 4, there are a variety of suitable methods for transmitting the file queue information to a workstation 421. For example, a user can request a file from the distribution module, and the distribution module can send the next file in the file queue to the user. As another example, the distribution process can push all or some of the files in a file queue to a user workstation, and the user workstation can automatically present the next file in a queue.

An optional queue replenishment module 421 can determine whether a user's file queue needs to be replenished. A number of thresholds for the queue decision module 421 are suitable for use herein. For example, a new file queue can be assembled after a previous file queue is pushed to the user's workstation. A new file queue can be assembled when there are a certain number of cases, for example, 10, 5, 1, or 0 cases, remaining to be sent to the user. The queue replenishment module 421 can determine that a user's file queue needs to be replenished at a particular time (e.g., every one or two hours). As another example, the queue replenishment module 421 can listen for a request to create and distribute a new queue. The request could come from a user, a workflow manager or superuser, or the prescreened data coordinator (not shown). The request could be sent, for example, via SSL (internet or intranet), e-mail, instant message, SMS text message, or the like. If the file queue needs to be replenished, then the above-described process begins again. The distribution module can append data files to an existing file queue, or the distribution module can create and distribute a new queue. This process can be repeated until halted or stopped or until a user quits or logs off a user workstation. Of course, even if the process is halted for one user, the process can continue for other users as needed.

Referring again to FIG. 3, the distribution module 112 can be configured to create a desired number of queues. For example, the distribution module 112 can create and/or distribute a file queue to a single user workstation, or the distribution module 112 can create and/or distribute file queues to a plurality of workstations. For example, the distribution module 112 shown in FIG. 3 distributes queue A 321 to workstation A 312, queue B 324 to workstation B 315, and queue C 327 to workstation C 318.

In some embodiments, the same prescreened data file can be distributed to more than one user for interpretation. This can advantageously create a competitive environment in which users compete against each other to make correct interpretations of prescreened data. This can also advantageously avoid inadvertent or intentional collaboration on interpreting prescreened data. In some embodiments, the same unscreened data file can be distributed to more than one user workstation for interpretation. This can advantageously allow a physician to survey multiple diagnostic clinicians for their interpretations of potentially challenging patient data.

A user workstation (e.g., workstation A 312) can be configured to cooperate with a local or remote queue module (not shown). A queue module can be configured to process a file queue (e.g., queue A 321) created and distributed by the distribution module 112. For example, a queue module be configured to serially present files in the queue on a first queued, first presented basis. A queue module can be configured to present files in a queue in other orders, such as randomly, according to certain predefined criteria, or dynamically according to received and/or learned events.

Figure 5:
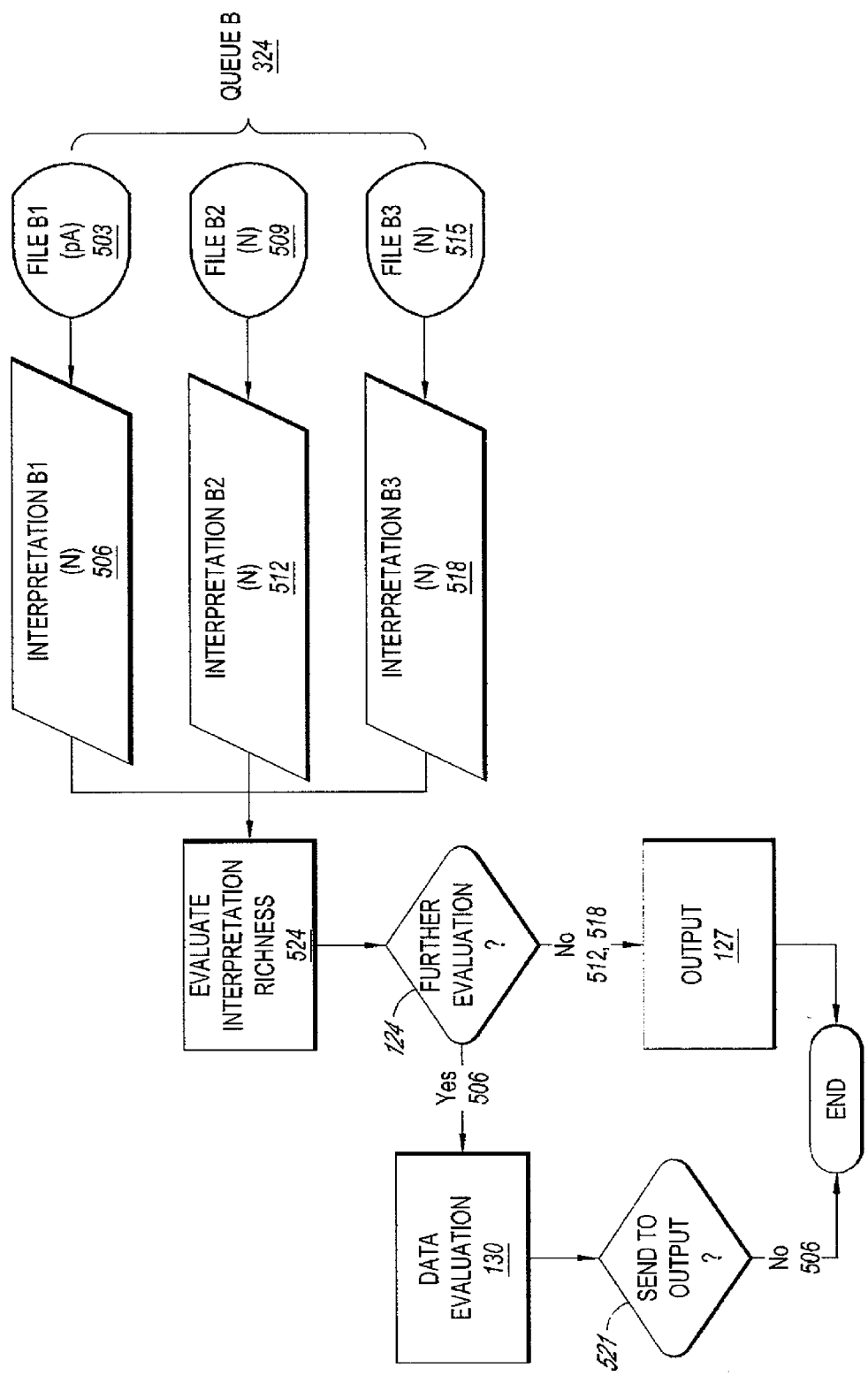
FIG. 5 illustrates processing of a file queue comprising prescreened data.

Referring to FIG. 5, a user interprets files (e.g., file B1 503, file B2, 509, and file B3 515) presented on the user workstation (not shown). The interpretations may be sent to system output 127, to a data evaluation module 130, or to both.

A user serially interprets the files in queue B 324. In this example, the user is first presented with file B1 (pA) 503, comprising an image showing a prescreened-abnormal condition.

In various embodiments, the origin of prescreened files can advantageously be "hidden" or "cloaked" from the user, such that the user cannot easily detect whether the file is prescreened or unscreened. Cloaking may be advantageous for training purposes or to improve accuracy and efficiency of data interpretation, as is explained below. Cloaking may be performed centrally, for example, for all files processed by the prescreened data coordinator. In some embodiments, cloaking may be performed on file-by-file basis.

Cloaking may be accomplished, for example, by changing, modifying, spoofing, or otherwise obfuscating file data. DICOM images, for example, comprise a file header (which stores information about the patient's name, the type of scan, image dimensions, etc), as well two- or three-dimensional image data. In some embodiments, the prescreened data coordinator (discussed above) can be configured to alter information in the data header (such as the study date, origin, etc.), which could alert a user that the data is prescreened.

Alternative cloaking mechanisms are also contemplated for use herein. For instance, cloaking may also be accomplished by masking data displayed on a user's workstation. A workstation processing DICOM files may display images along with textual portions comprising patient information on the data display. In some embodiments, the workstation can be configured to detect whether a file is prescreened and display a text box containing falsified patient data. The text box can overlay the original textual portions in a way that in undetectable by the user. The data in the text may be obtained from the prescreened data coordinator, the data distributor, or from some other source, as needed.

Referring again to FIG. 5, the user (unaware that file B1 503 is not ordinary production workflow data) incorrectly interprets file B1 503 as comprising normal data. The user enters incorrect interpretation B1 (N) 506 at the workstation.

Detecting that the interpretation was based upon prescreened data, the decision module 124 (discussed above with respect to FIG. 1) can direct that the incorrect interpretation B1 (N) 506 be transmitted to a data evaluation module 130 for additional processing. The data evaluation module 130 preferably comprises an output evaluation module 521 configured to determine whether the data should be sent to the system output 127, such as a CIS or HIS. Because file B1 (pA) 503 is not ordinary production workflow data but rather prescreened abnormal data, it may not be desirable to send incorrect interpretation B1 (N) 506 to the system output 130, as shown in FIG. 5. Accordingly, the output evaluation module 521 can evaluate whether file B1 (pA) 503 was flagged as prescreened or otherwise marked for restriction from the system output. Of course, other evaluation methods are also suitable. Furthermore, it may be desirable to send prescreened data to the system output in certain embodiments.

Figure 6A:
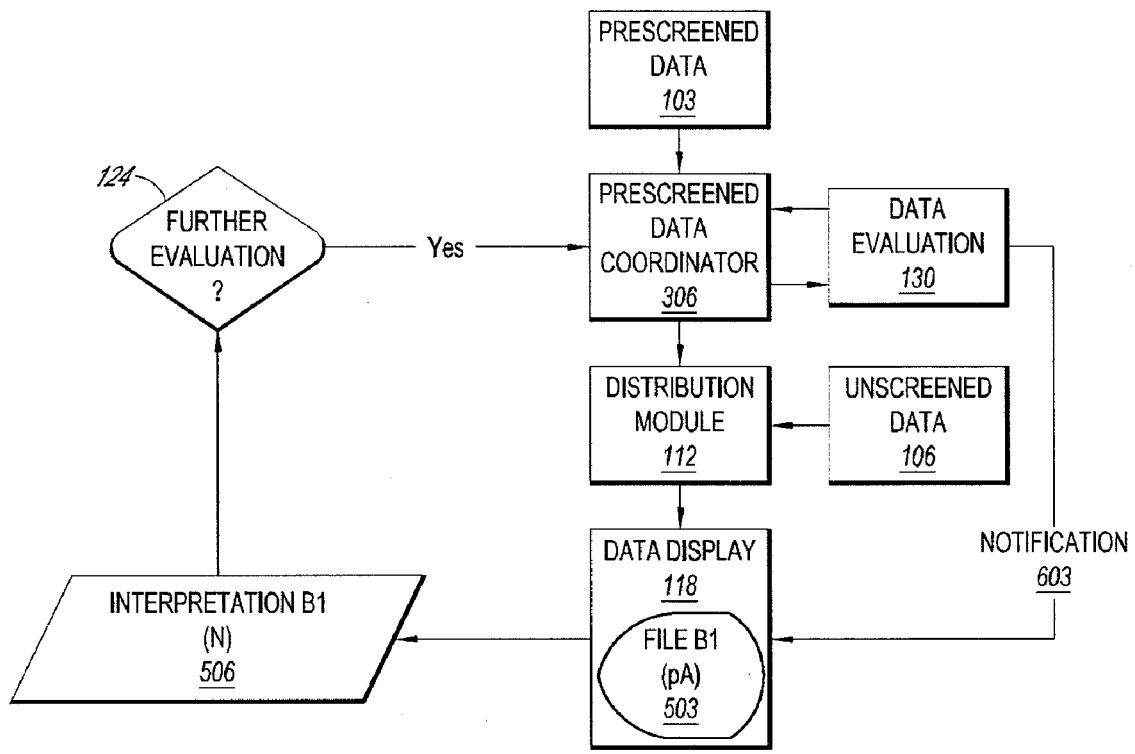
FIG. 6A and FIG. 6B illustrate providing notification for the interpretation of prescreened data.
Figure 6B:
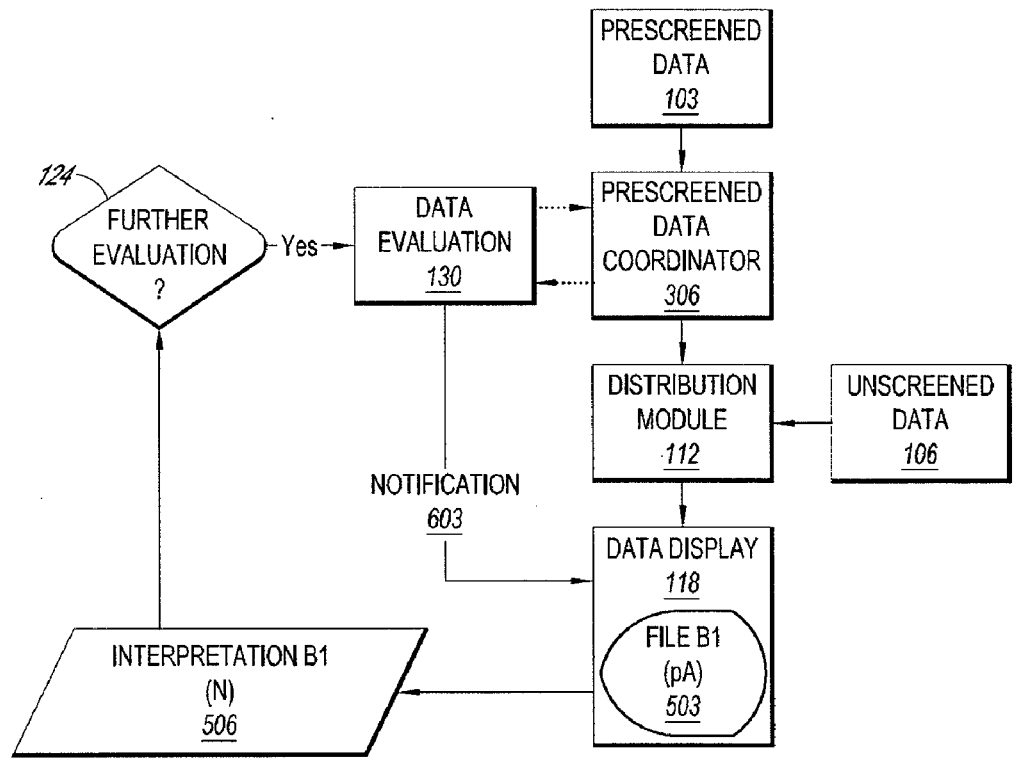

The user may be immediately notified of an incorrect or correct interpretation or notified at a later time. Notification may advantageously help the user to learn and to not make the same or similar mistake again. Immediate notification may help the user to learn in real-time. Example methods for providing notification are shown in FIG. 6A and FIG. 6B. Of course, alternative methods are suitable for use herein and are contemplated by this disclosure.

Referring first to FIG. 6A, a file B1 (pA) 503, comprising a prescreened-abnormal condition, is presented to the user via data display 118. The user incorrectly interprets file B1 503 as showing only normal data. The user enters incorrect interpretation B1 (N) 506 at the workstation. Decision module 124 ascertains that interpretation B1 (N) 506 was based on a prescreened file and determines that further evaluation is needed.

Still referring to FIG. 6A, the user's interpretation B1 (N) 506 may be transmitted to prescreened data coordinator 306. The prescreened data coordinator 306 can access the desired interpretation (abnormal) based on the results of the prescreening and transmit the information to the data evaluation module 130, which is configured to compare the user's interpretation B1 (N) 506 with the desired interpretation.

The prescreened data coordinator 306 can subsequently transmit a notification 603 based on the comparison to the user's data display 118. In some embodiments, the data evaluation module 130 can transmit certain data back to the prescreened data coordinator 306. The data coordinator 306 can store the user's interpretation B1 (N) 506, store the data evaluation module 103 comparison, and/or store whether the user interpretation was correct or incorrect, for example, in a user profile table. This information can be later downloaded by the user's manager and used in the user's performance review or transmitted to the user via notification 603 at a later time (e.g., at the end of a user's shift). In some embodiments, this information can be utilized by the distribution module 112 when deciding whether to display the file to the user at a later time.

An alternative method for providing notification is shown in FIG. 6B. The process is similar to the one described above with respect to FIG. 6A, however, FIG. 6B demonstrates that the prescreened data coordinator 306 is not needed in order to provide notification to a user. For example, the desired interpretation can be embedded in a prescreened file (e.g., in the metadata or in the header data). This embedded data is not ordinarily visible to or easily accessible by the user. However, the embedded data can be displayed to the user, e.g., via a pop-up box or other display mechanism, if the decision module 124 determines that a file was prescreened or otherwise needs further evaluation. As shown in FIG. 6B, however, the user's interpretation is optionally but desirably communicated to the prescreened data coordinator 306. The prescreened data coordinator 306 can retain the data for later review or for distribution instruction purposes.

In some embodiments, the prescreened data coordinator 306 may be used to monitor and the correctness of a user's interpretations of prescreened data. When a user's accuracy falls below a certain percentage or the user makes a certain number of consecutive mistakes, the prescreened data coordinator 306 can notify the user to take a break. In some embodiments, the monitoring notification can be configured to "lock out" the user's access to user input during the break. Monitoring notification can comprise a message or report that may be communicated to the user. Preferably, the monitoring notification is transmitted to the user immediately before any additional files are presented for interpretation. However, the message or report can be delivered after a delay. However, in embodiments that do not comprise a prescreened data coordinator 306, other system elements, such as a server (e.g., server 112 shown in FIG. 1) or distribution module 112, can also perform monitoring.

Injecting prescreened data into a workflow and monitoring users' interpretation of prescreened data may allow enhancing the use of data analysis and data mining capabilities of the workflow. Data analysis and data mining comprise a variety of powerful numerical, statistical, probabilistic, algorithms and methods and the like that operate on data sets. Data analysis and data mining may be used to improve, forecast, and predict users' accuracy and efficiency. For example, a user's accuracy and efficiency can be increased by creating a working schedule that decreases mistakes due to fatigue, such as scheduling periodic breaks to maintain a desired level of interpretational accuracy. A user may make few mistakes when processing data early in the shift, and may require infrequent breaks to maintain a desired level of interpretational accuracy. By monitoring a user's accuracy over the course of a workday, the frequency and length of breaks may be increased to maintain a desired level of interpretational accuracy. As another example, a user's accuracy and efficiency may be improved by scheduling periodic training, and the training can be further custom tailored to the user's needs.

Referring again to FIG. 5, when the user is finished interpreting file B1 (pA) 503, the user is next presented with file B2 (N) 509, an unscreened file comprising normal data. The user correctly enters interpretation B2 (N) 512, which is subsequently sent to system output 127. This process is repeated for file B3 (N) 518.

As shown in FIG. 5, in some embodiments, the richness of a user's interpretation can be evaluated and/or monitored. As explained in more detail below, interpretive output information may be dynamically monitored and learned, and this advantageously may allow for flexible, real-time, "on-the-fly" adjustments of the amount and/or characteristics of prescreened data presented to users.

A user's interpretation can be assigned a rank, score, or the like. Medical images which denote normal anatomy or lack of findings (normal diagnosis) may be assigned neutral or negative scores. Images which denote normal variants may be assigned low positive scores, and images of abnormal anatomy or pathology may be assigned increasingly higher positive scores depending upon the seriousness of the finding. For example, "lung fields are clear" may be assigned a score of zero or a negative score. "Infiltrate" may be assigned a score of one. "Pleural Effusion" may be assigned a score of three. "Subdiaphragmatic Air," a serious sign of a ruptured bowel or stomach, may be assigned a score of seven. "Pneumothorax," or collapse of the lung, may be assigned a score of six. "Tension Pneumothorax," a more severe collapse of the lung with actual displacement of the lung, may be assigned a score of ten. "Calcified Nodule" in the context of the lung may be assigned a score of three but in the context of a mammogram may be assigned a score of eight. As another example, "Displaced Fracture" may be assigned a score of three. "Non-displaced Fracture" may be assigned a score of two. "Foreign Bodies" would be assigned a score of five. "Surgical Sponge" would be assigned a score of ten.

The above examples are provided for illustrative purposes only. Of course, alternative scoring systems in which increasingly serious diagnoses or interpretations are numerically distinguished from routine or non-serious diagnoses are also contemplated in this disclosure. In some embodiments, very rich, difficult, or rare diagnosis data may be assigned a lower score than simple data, which is assigned a higher score. Furthermore, more sophisticated scoring algorithms can also be used. A score can be assigned for both prescreened data and unscreened data in certain embodiments. Alternatively, the score can be assigned only for prescreened data or only for unscreened data. The score can be assigned for a subset of any of the above-mentioned data sets as well.

The system may also track an aggregated score. The aggregated score can be related to the arithmetic sum, the moving average, or some other aggregation of the user's scores over time. According to the user's aggregated score, more or less prescreened data may be presented to the user. For example, if a user's interpretive output rank score is high (meaning that the user is interpreting a large volume of rich or difficult data), less prescreened data may be presented to the user. A rapidly increasing score may indicate that the user is suddenly interpreting large volumes of rich or difficult workflow data, such as during a natural disaster, epidemic, terrorist attack, war, or other event that creates large volumes of rich or difficult production workflow data. Accordingly, the system may temporarily stop the distribution of prescreened data to the user. As another example, if a user's aggregated score is high, the user's schedule may be adjusted such that the user should take more frequent breaks, longer breaks, or works shorter shifts to maintain a desired level of interpretive accuracy. As another example, if a user's interpretative score is high, a second examination of particularly difficult interpreted data may be needed, and the data may be marked or flagged accordingly, as is described above.

Scoring of a user's interpretation may in some embodiments trigger or otherwise affect reporting of the output. Because the score can be indicative of the degree of richness or the seriousness of diagnosis of unscreened data, it may be desirable to communicate the score and/or the associated interpretation with the "outside world," such as to an entity, a case review committee, a peer review committee, a government agency, the requesting physician, or the like. In some embodiments, the unscreened data coordinator may communicate the score and/or the interpretation, however, a variety of modules, servers, or modules are suitable for this purpose. The communication may be performed by sending an Internet request, email message, instant message, SMS text message, or the like.

In some embodiments, it may be desirable to solicit feedback relating to the richness or difficulty of a user's interpretation before ranking or scoring the interpretation. A user may seek real-time advice (e.g., via a face-to-face dialogue, a telephone conversation, instant messaging, chat, or the like) to determine the richness or difficulty. The advice may be sought internally (e.g., from output, or unscreened prescreened data coordinator, or the like) or externally (e.g., by sending an Internet request, email message, instant message, SMS text message, or the like to an external party). Accordingly, various embodiments comprise means for soliciting feedback regarding a user's interpretation.

Figure 7:
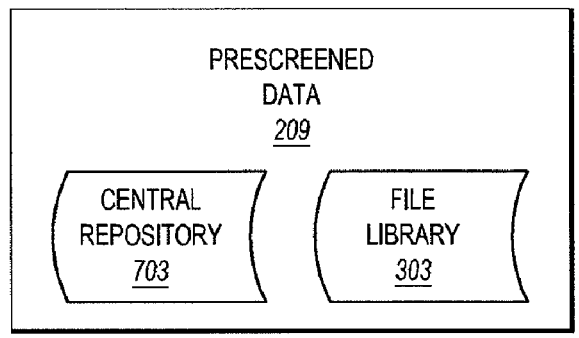
FIGS. 7 and 8 is a block diagram illustrating the integration of a central repository into a workflow.

Referring now to FIG. 7, certain embodiments may comprise a central repository 703 as a source of prescreened workflow data. In contrast to a file library 303 (discussed above), a central repository 303 is configured to both send and receive prescreened data. A central repository may be used in conjunction with the file library, or may be used without the file library. FIG. 7 illustrates a central repository 703 of prescreened data 209 in conjunction with a file library 403. A central repository 703 can be located on the same computer as the file library 303 or on a different local or remote computer.

Because a central repository permits both sending and receiving of prescreened data, a central repository 703 can allow different networks to "pool" and/or share their prescreened data together. The central repository 703 may advantageously provide these networks greater access to prescreened data than each network would have on its own. This feature can advantageously allow a network to create a commercially valuable source of prescreened data that can be sold as a file library to other users.

Figure 8:
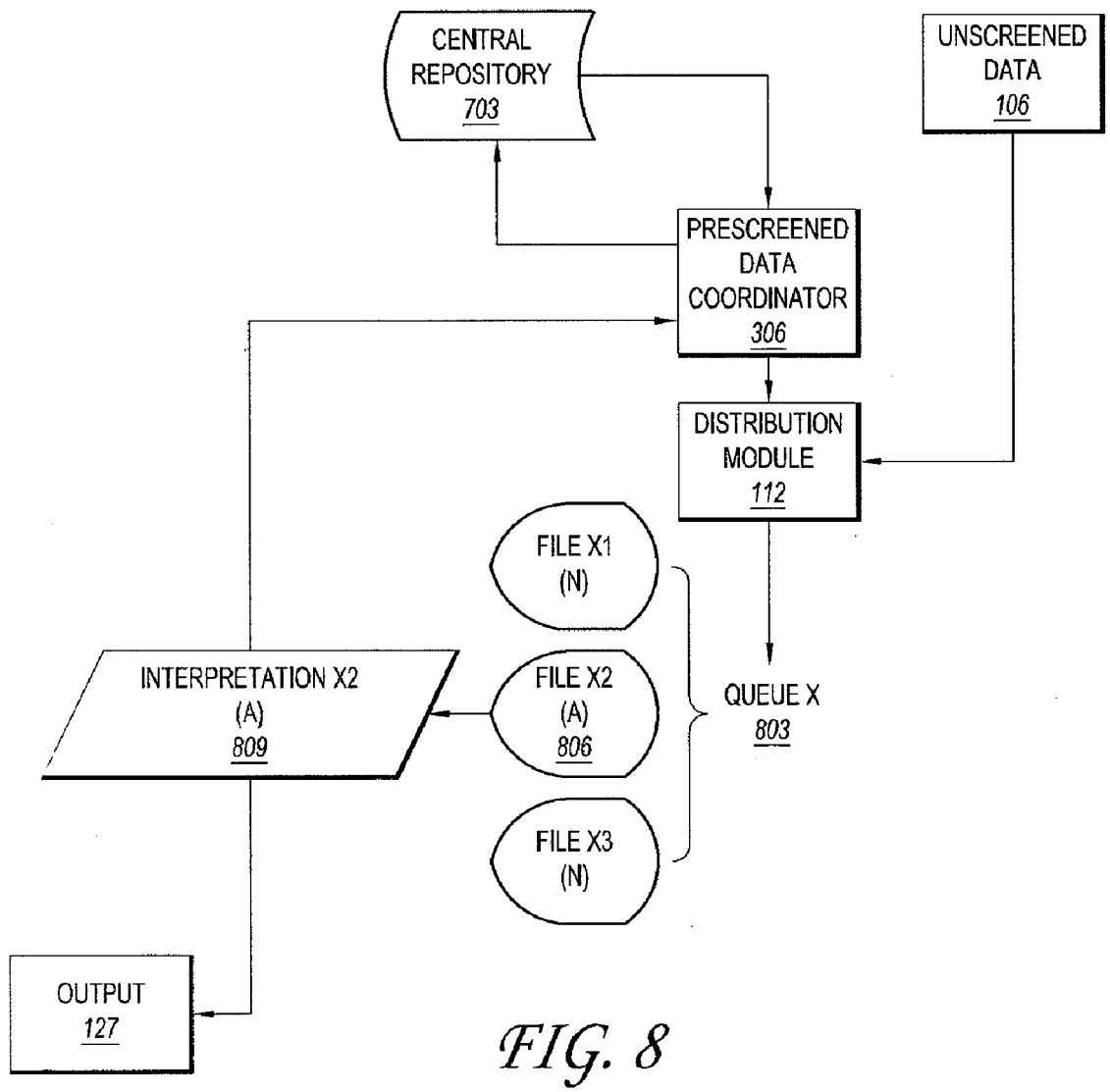

FIG. 8 illustrates how a central repository 703 can be integrated into a workflow. The distribution module 215 receives data from the prescreened data coordinator 406 and the source of unscreened data 106. The data are distributed into queue X 803. The second file in the queue, file X2 (A) 806 comprises abnormal data. The user makes correct interpretation X2 (A) 809, and interpretation X2 (A) 809 is sent to the system output 127.

The user may then flag the file for insertion into the central repository 712. Alternatively, the insertion may take place without any action by the user. Interpretation X2 (A) 809 is sent to the prescreened data coordinator 306. The prescreened data coordinator 306 can transmit file X2 (A) 806 and/or the associated interpretation X2 (A) 809 to the central repository 712.

File X2 (A) 806 can subsequently be used as a prescreened file in a workflow, and its associated interpretation X2 (A) 709 may optionally be used as the desired interpretation for comparison purposes. The central repository 703 can communicate file X2 (A) 806 to the prescreened data coordinator 306. As explained above, the data can subsequently be distributed by a distribution module 112 for presentation to users.

Figure 9:
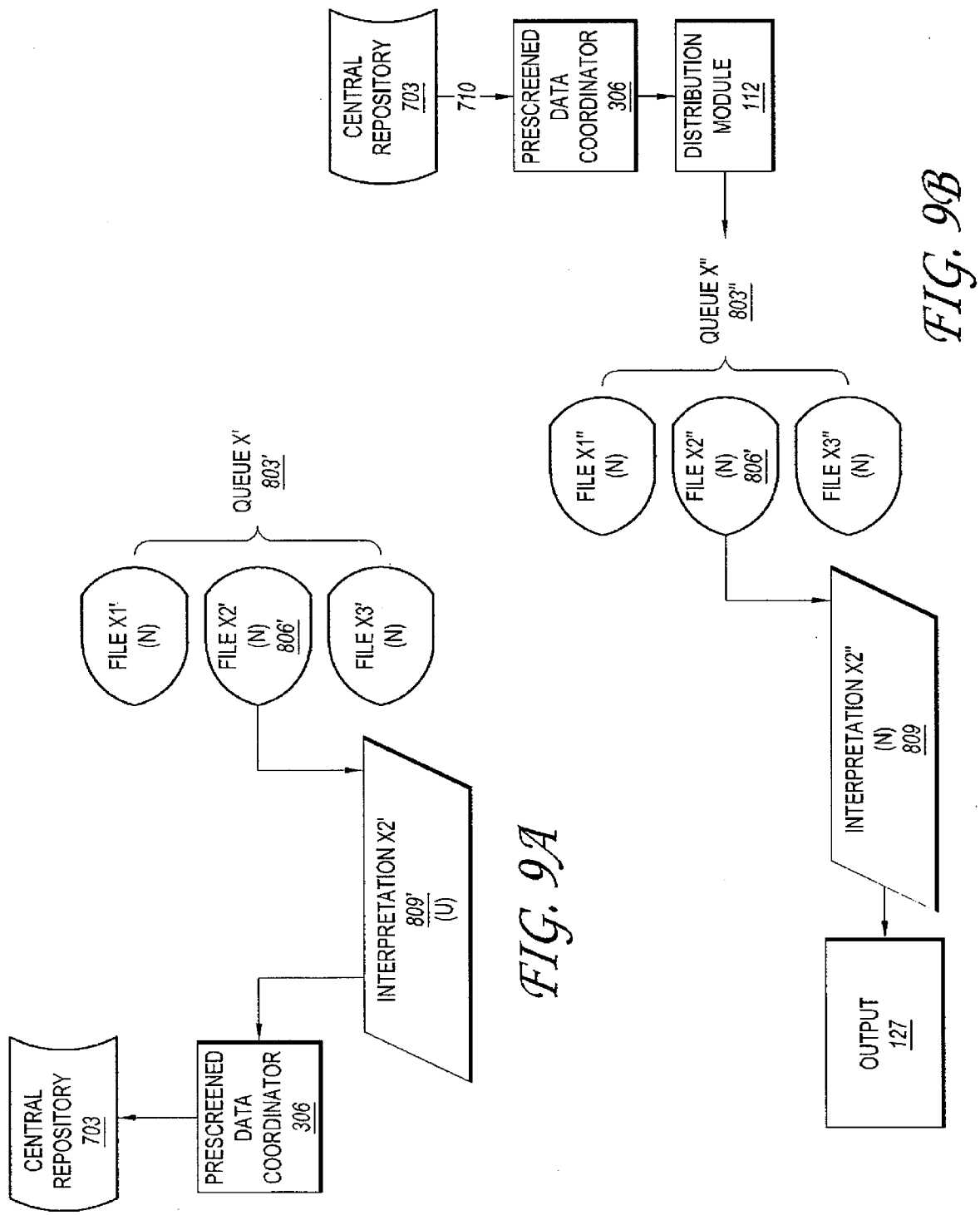
FIG. 9A and FIG. 9B illustrate using a central repository for facilitating a consensus or collaborative diagnoses.

FIG. 9A and FIG. 9B show that the central repository 703 can be useful for facilitating consensus or collaborative diagnoses. A user processes queue X' 803'. The user is presented with file X2' (N) 806', an image showing an unscreened normal condition. In this example, the user is unsure whether file X2' (N) 806' comprises normal or abnormal conditions. Accordingly, the user enters that the condition is "unknown" and generates interpretation X2' (U) 809' at the workstation. In some embodiments, the user can alternatively or in conjunction mark or flag the file for follow-up interpretation. The file is transmitted via data coordinator 306 to the central repository 712.

Later the file X2' (N) 806' is distributed to new queue X" 803" by the distribution module 112 after it is received from the central repository 703 by way of the data coordinator 406. Data interpreted as "unknown" may be presented to a new user or the same user for another attempt at the interpretation. In this example, a new user is presented with file X2' (N) 806'. In this example, the user evaluates the image, correctly decides X2' (N) 806' comprises normal data, and generated interpretation X2" 809" at the workstation.

The interpretation X2" 809" is sent to the system output 127 for subsequent communication to an ordering physician and patient. The image may be untagged as "unknown," and tagged as diagnosed. Alternatively, the "unknown" tag may be maintained for subsequent users' attempts at the interpretation (e.g., to achieve a consensus diagnosis).

In some embodiments it may be advantageous for the user to receive "feedback" during or after interpretation of prescreened or unscreened data. The workflow user has an interest in ensuring his or her interpretation is received by the ordering physician. The user may also require additional feedback from the ordering physician. Based on the user's interpretation, the ordering physician may provide additional relevant clinical information to the user or the ordering physician may take issue with the final interpretation.

In certain embodiments, the user may want to notify the ordering physician on an urgent basis of the criticality of the findings reported. There are various degrees of criticality ranging from immediate notification to verifying receipt of the interpretation. Data presented to the user may be flagged or marked for feedback. Based upon the criticality, the system may require a response to be lodged either electronically, by interactive voice response, voicemail, paging, text messaging, direct voice access, or other means for notification. Receipt of the notification may be acknowledged by the means for notification.

Based upon the criticality of the findings, a watchdog timer could be established within which time frame a response would be expected. If the response is not received, the selected means for notification could be escalated to a more direct form of communication to ensure that the findings were timely conveyed.

Figure 10:
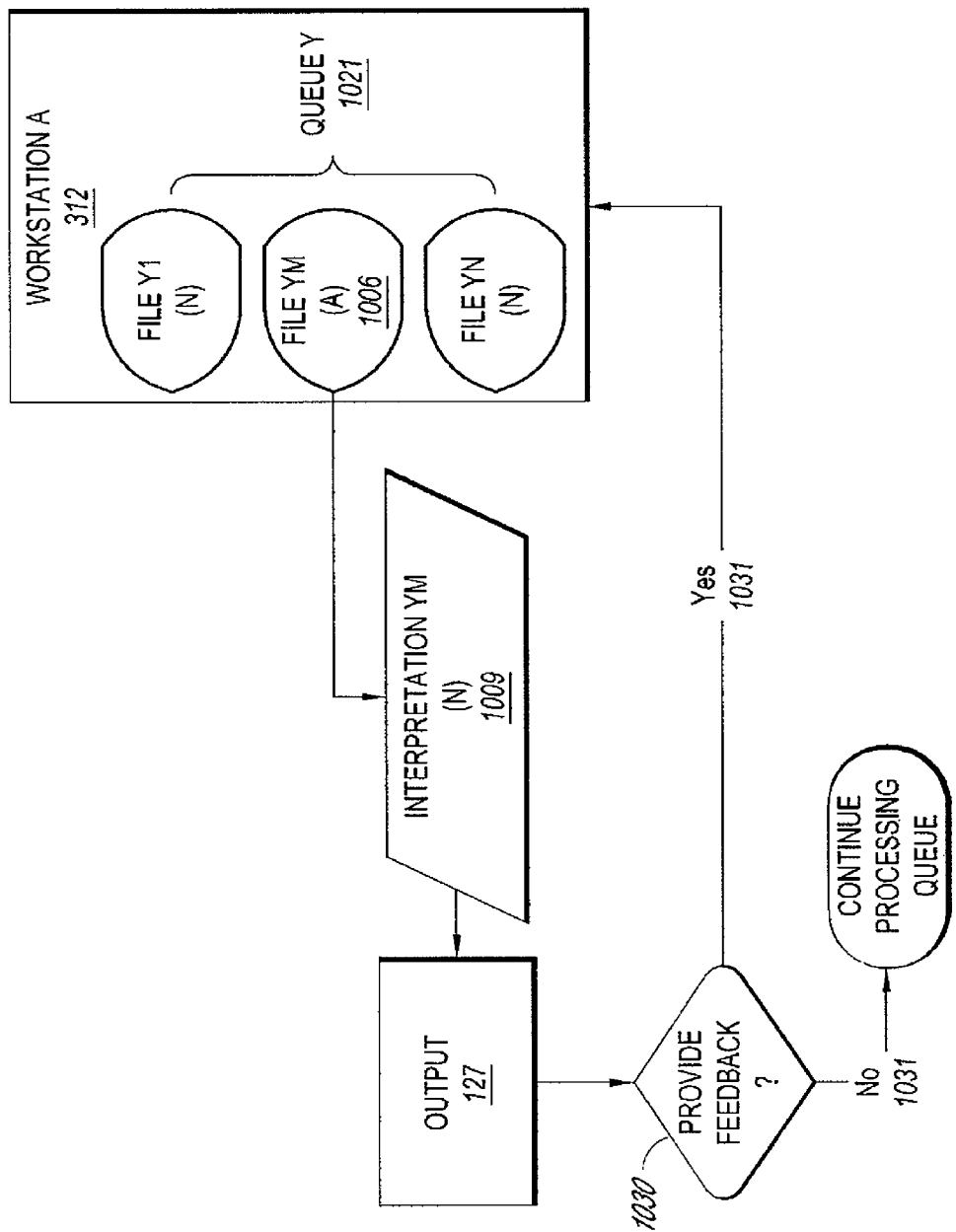
FIG. 10 illustrates provision of feedback to the user.

Example methods for providing feedback are shown in FIG. 10. Of course, alternative methods are suitable for use herein and are contemplated by this disclosure.

As shown in FIG. 10, a user processes queue Y 1021. The user is presented with file YM 1006, and makes an interpretation YM 1009. The interpretation YM 1009 is sent to the system output 127 for subsequent communication to an ordering physician. Subsequently, the interpretation is sent to the feedback module 1030, which can be configured to determine whether the interpretation has been flagged for feedback. The feedback module determines whether the ordering physician needs to provide feedback or whether the queue processing may resume. If feedback needs to be provided, the feedback module determines its type (based on the level of criticality), and provides the appropriate feedback.

A wide variety of variations are possible. Components may be added, removed, or reordered. Different components may be substituted out. The arrangement and configuration may be different. Similarly, processing steps may be added or removed, or reordered. Those skilled in the art will appreciate that the methods and designs described above have additional applications and that the relevant applications are not limited to those specifically recited above. For example, several example embodiments discussed herein are presented in the context of medical treatment. However, the disclosure can be implemented in a wide variety of workflows in many types of industries, e.g., test and manufacturing, business processes, travel, security, etc. Furthermore, it is contemplated that this disclosure relates to virtual workflows, e.g., workflows used in non-production capacities. The users of the system can be, for example, students accessing and processing a simulated workflow via a LAN, WAN, or the Internet. In these embodiments, training data can come from a variety of sources, e.g., a central repository, a file library, and/or modalities. Also, the present invention may be embodied in other specific forms without departing from the essential characteristics as described herein. The embodiments described above are to be considered in all respects as illustrative only and not restrictive in any manner.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A system for processing medical image files comprising:
a plurality of databases;
an unscreened files module configured to access unscreened medical image files from the plurality of databases, wherein the unscreened medical image files are created by at least one imaging modality and have not been previously diagnosed, such that medical conditions associated with the unscreened medical image files are not known by the system or the system user;
a prescreened files module configured to access prescreened medical image files from the plurality of databases, wherein the prescreened files comprise images that are associated with one or more medical conditions that have been previously diagnosed other than by the system user and the diagnoses are known by the system but not by the user;
a distribution module comprising a selection processor configured to select files from the unscreened files module and the prescreened files module and a transmission processor configured to transmit the files to the user's workstation in a predetermined ratio;
a system monitoring module configured to monitor and evaluate the user's interpretive output information of the unscreened and prescreened files, wherein the monitoring and evaluation comprises applying ranking algorithm to the interpretive output information to produce a cumulative rank; and
a distribution override processor in communication with the system monitoring module and the selection processor, wherein the distribution override processor is configured to adjust, based on the cumulative rank, at least one of the ratio of unscreened medical image files to prescreened medical image files, and characteristics of prescreened medical image files transmitted to the workstation, wherein, as the cumulative rank becomes greater, the ratio of unscreened medical image files to prescreened medical images files becomes lower.

2. The system of claim 1, wherein monitoring and evaluating a user's interpretive output information comprises determining the level of difficulty in diagnosing a prescreened and/or unscreened file.

3. The system of claim 1, wherein monitoring and evaluating a user's interpretive output information comprises determining the number of medical image files for which the user generates interpretive output information over time.

4. The system of claim 1, wherein monitoring and evaluating a user's interpretive output information comprises determining the severity of the one or more medical conditions associated with a prescreened and/or unscreened file.

5. The system of claim 1, wherein the characteristics of prescreened medical images are related to the one or more medical conditions associated with the prescreened medical image file.

6. The system of claim 1, wherein origination data in the prescreened medical image files are altered in such a way that each of the prescreened medical image files appears to be similar to an unscreened medical image file when viewed by the user.

7. The system of claim 1, wherein a greater rank is represented by a lower number.

8. A system for processing medical files comprising:
an unscreened files module configured to access unscreened medical image files from one or more databases, wherein the unscreened files have not been previously diagnosed, such that medical conditions associated with the unscreened medical image files are not known by the system or the system user;
a prescreened files module configured to access prescreened medical files from one or more databases, wherein each prescreened file is associated with a predetermined diagnosis that has been previously determined by another as being associated with one or more medical conditions, such that the diagnoses are not known by the user;
a distribution module comprising a selection module configured to select files from the unscreened files module and the prescreened files module, and further comprising a transmission module configured to transmit the files to the user such that the files are viewed by the user in a predetermined ratio of unscreened files to prescreened files; and
a system monitoring module configured to assign a rank to the user's interpretive output information of the unscreened and prescreened files and, based on the rank:
adjust the ratio of unscreened medical files to prescreened medical files viewed by the user, wherein, as the rank becomes lesser, the ratio of unscreened medical image files to prescreened medical images files becomes higher; or
adjust the difficulty of and/or the severity of the one or more medical conditions associated with the prescreened medical files viewed by the user, wherein, as the rank becomes lesser, the difficulty and/or severity becomes higher; or
instruct the user to stop reviewing files for a time when the rank lessens to a predetermined deficiency level.

9. The system of claim 8, wherein the rank comprises a neutral, a positive, or a negative number.

10. The system of claim 8, wherein a user's interpretive output information relating to an unscreened medical image of abnormal anatomy or pathology is assigned an increasingly higher positive rank depending upon the severity of the medical conditions identified in the user's interpretative output information.

11. The system of claim 8, wherein a user's interpretive output information is assigned an increasingly higher positive rank depending on the difficulty and/or seriousness of the medical conditions identified in the user's interpretive output information.

12. The system of claim 8, wherein a lesser rank is represented by a higher number.

13. A method for processing medical files comprising:
  accessing unscreened medical files from one or more databases, wherein the unscreened files have not been previously diagnosed as being associated with one or more medical conditions, such that the medical conditions associated with the unscreened medical files are not known by the system or the system user;
  accessing prescreened medical files from one or more databases, wherein the prescreened files are associated with predetermined diagnoses of one or more medical conditions that are not known by the user;
  transmitting the accessed files to the user's workstation such that the files are viewed by the user in a predetermined ratio of unscreened files to prescreened files;
  ranking the user's interpretive output information of the unscreened files and prescreened files; and, based on the rank:
    adjusting the ratio of unscreened medical files to prescreened medical files transmitted to the user's workstation, wherein, as the rank becomes lesser, the ratio of unscreened medical image files to prescreened medical images files becomes higher; or
    adjusting the level of difficulty of and/or the severity of the one or more medical conditions in the prescreened medical files transmitted to the user's workstation, wherein, as the rank becomes lesser, the difficulty and/or severity becomes higher; or
    instructing the user to stop reviewing files for a time when the rank lessens to a predetermined deficiency level.

14. The method of claim 13, wherein ranking comprises parsing the interpretive output information for keywords.

15. The method of claim 13, wherein ranking comprises locating previously defined numeric values associated with keywords in the interpretive output information in a database, and calculating a rank of the interpretive output information based on the numeric values.

16. The method of claim 13, wherein adjusting or instructing based on the rank is based on an aggregated rank.

17. The method of claim 13, wherein adjusting or instructing based on the rank is based on an arithmetic sum, moving average, or other aggregation of the user's ranks over time.

18. The method of claim 13, wherein a lesser rank is represented by a higher number.

* * * * *